(12) United States Patent  (10) Patent No.: US 8,915,851 B2
Kim  (45) Date of Patent: Dec. 23, 2014

(54) ULTRASOUND IMAGING APPARATUS AND METHOD OF DISPLAYING ULTRASOUND IMAGE

(71) Applicant: Samsung Electronics Co., Ltd., Suwon-si, Gyeonggi-do (KR)

(72) Inventor: Kang Sik Kim, Seongnam-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 0 days.

(21) Appl. No.: 13/692,390

(22) Filed: Dec. 3, 2012

(65) Prior Publication Data

US 2013/0144150 A1  Jun. 6, 2013

(30) Foreign Application Priority Data

Dec. 5, 2011  (KR) .................. 10-2011-0129079

(51) Int. Cl.
*A61B 8/00* (2006.01)
*A61B 5/00* (2006.01)
*A61B 8/08* (2006.01)

(52) U.S. Cl.
CPC .............. *A61B 5/0095* (2013.01); *A61B 5/742* (2013.01); *A61B 2562/02* (2013.01); *A61B 8/0816* (2013.01); *A61B 8/4281* (2013.01); *A61B 5/7278* (2013.01); *A61B 5/0053* (2013.01); *A61B 5/743* (2013.01)
USPC ............ 600/437; 600/442; 600/473; 600/476

(58) Field of Classification Search
USPC .................... 600/437–469, 473–480
See application file for complete search history.

(56) References Cited

U.S. PATENT DOCUMENTS

| 7,946,180 | B2 * | 5/2011 | Sumi .............................. 73/789 |
| 2005/0070803 | A1 * | 3/2005 | Cullum et al. ................ 600/473 |
| 2010/0049044 | A1 | 2/2010 | Burcher |
| 2010/0331662 | A1 | 12/2010 | Fukutani et al. |
| 2012/0271170 | A1 * | 10/2012 | Emelianov et al. ........... 600/439 |
| 2012/0278005 | A1 * | 11/2012 | Sumi .............................. 702/43 |
| 2013/0338498 | A1 * | 12/2013 | Emelianov et al. ........... 600/431 |

FOREIGN PATENT DOCUMENTS

JP  2010-88499  4/2010
JP  2011-206192  10/2011

OTHER PUBLICATIONS

International Search Report dated Feb. 8, 2013 in International Patent Application No. PCT/KR2012/010442.

* cited by examiner

*Primary Examiner* — Sanjay Cattungal
(74) *Attorney, Agent, or Firm* — Staas & Halsey LLP

(57) ABSTRACT

An ultrasound imaging apparatus and ultrasound image display method simultaneously obtain photo-acoustic information and elasticity information of a subject, and generate and display a single image having the photo-acoustic information and the elasticity information, thereby enhancing accuracy and efficiency of a diagnosis. The ultrasound imaging apparatus includes a probe to radiate light when stress is applied and when stress is not applied to the subject, and to receive a corresponding first acoustic wave signal and a second acoustic wave signal, a data acquisition unit to acquire first acoustic wave data and second acoustic wave data that each represent optical absorption rate information about the subject, an elasticity information generating unit to calculate elasticity information about the subject, an image generating unit to generate a single image having both of the optical absorption rate information and the calculated elasticity information, and a display unit to display the generated image.

22 Claims, 17 Drawing Sheets

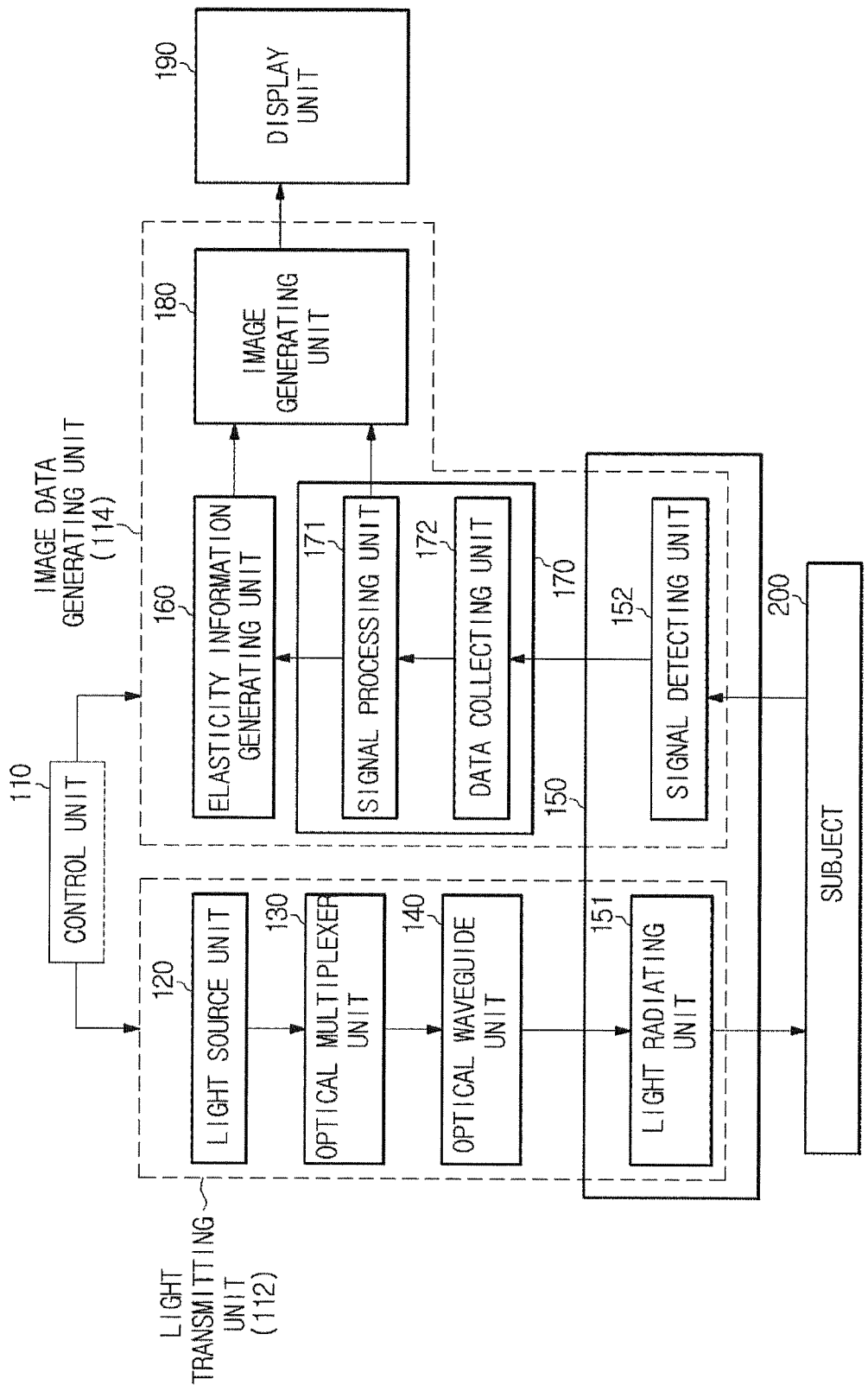

ULTRASOUND IMAGING APPARATUS AND METHOD OF DISPLAYING ULTRASOUND IMAGE

CROSS-REFERENCE TO RELATED APPLICATIONS

This application claims the priority benefit of Korean Patent Application No. 10-2011-0129079, filed on Dec. 5, 2011, in the Korean Intellectual Property Office, the disclosure of which is incorporated herein by reference.

BACKGROUND

1. Field

Embodiments disclosed herein relate to an ultrasound imaging apparatus configured to simultaneously obtain ultrasound elasticity information and photo-acoustic information on a subject, and a control method thereof.

2. Description of the Related Art

PAT (Photo Acoustic Tomography) is a technology suitable for imaging a tissue of a body by using a method of combing a high spatial resolution of an ultrasound image with a high optical contrast of an optical image. As a laser is radiated on a tissue of a living body, the short electromagnetic pulse of the laser is absorbed into the tissue of the body, and thus a temporary acoustic pressure is generated by the thermo-elastic expansion at a portion of the tissue that acts as the source at which the initial ultrasound wave is generated. The ultrasound waves formed as such are reached at the surface of the tissue of a body at various intervals of delays, and the imaging of such is referred to as a photo-acoustic image.

The ultrasound imaging technology is an established medical imaging technology configured to diagnose a lesion inside a human body by using an ultrasound wave. An ultrasound image is mostly displayed as a B-mode image that uses the coefficient of reflection according to the difference of the impedance between the tissues. However, for a tumor or a cancer lesion, a portion may exist having no difference in the coefficient of reflection compared to the surrounding tissues, and therefore such portions may not be distinguishable on the B-mode image. On the contrary, ultrasound elastography, which images the mechanical characteristics of a tissue, provides considerable assistance in diagnosing a lesion such as a cancer tissue. By using the characteristic that, when an outside force is applied to deform a tissue, a hard tissue such as cancer has a small displacement in the direction of the force applied, and a soft tissue has a large displacement in the direction of the force applied, a diagnosis may be made whether the lesion of the tissue is cancer, and the method as such is referred to as an ultrasound elasticity imaging method.

The ultrasound elastography method may be capable of determining the characteristic value (the stiffness) of the tissue itself. Thus, this method may be useful in the diagnosis of a tumor that is generated in a relatively uniform medium such as breast cancer or prostate cancer. Therefore, a surgical procedure, such as a biopsy that causes an inconvenience of a patient, may be reduced, and thereby the usefulness of the ultrasound elastography method may be significant.

Since the photo-acoustic imaging method and the ultrasound elasticity imaging method are capable of distinguishing a lesion tissue and a normal tissue, respectively, both methods may be used for a purpose such as an early diagnosis of cancer. If the photo-acoustic imaging method and the ultrasound elasticity imaging method are simultaneously used, the accuracy of a diagnosis may be further enhanced.

Suggested methods to simultaneously use photo-acoustic image information and ultrasound elasticity image information include a method of displaying a photo-acoustic image and an ultrasound elasticity image by obtaining each of the photo-acoustic image and the ultrasound elasticity image, and a method of matching a photo-acoustic image and an ultrasound elasticity image by obtaining each of the photo-acoustic image and the ultrasound elasticity image. However, to simultaneously use photo-acoustic image information and ultrasound elasticity image information in the above methods, each of the images is separately needed to be obtained, and thus inefficiencies result in terms of the test time and the cost of the tests, and also, an error may occur when the two images are matched.

SUMMARY

Therefore, it is an aspect of the present invention to provide an ultrasound imaging apparatus configured to enhance the accuracy and the efficiency of a diagnosis by simultaneously obtaining photo-acoustic information and elasticity information about a subject through the ultrasound imaging apparatus, and by generating and displaying a single image having both information, and a control method thereof.

Additional aspects of the disclosure will be set forth in part in the description which follows and, in part, will be obvious from the description, or may be learned by practice of the disclosure.

In accordance with one aspect of the present disclosure, an ultrasound imaging apparatus includes a probe, a data acquisition unit, an elasticity information generating unit and an image generating unit. The probe may be configured to radiate light having a particular wavelength component to a subject in a state when a stress is applied to the subject and in a state when a stress is not applied to the subject, and configured to receive a first acoustic wave signal that is generated when a stress is not applied to the subject and a second acoustic wave signal that is generated when a stress is applied to the subject. The data acquisition unit may be configured to acquire a first acoustic wave data and a second acoustic wave data that each represent optical absorption rate information about the subject, by processing the first acoustic wave signal and the second acoustic wave signal that are received from the probe. The elasticity information generating unit may be configured to calculate elasticity information about the subject by comparatively analyzing the first acoustic wave data and the second acoustic wave data. The image generating unit may be configured to generate a single image having both of the optical absorption rate information, which is expressed as the acoustic wave data, and the calculated elasticity information. The display unit may be configured to display the image generated by the image generating unit.

The image generating unit, by using a color map, may be configured to perform a mapping of a color that corresponds to each of the optical absorption rate information and the elasticity information of a tissue that forms the image.

The mapping of the color may be performed in pixel units.

The color map may be composed in a way that the color in a direction of one axis is varied according to the optical absorption rate information, and the color in a direction of another axis is varied according to the elasticity information.

The color map may be composed in a way that the color is varied in a direction of one axis according to the optical absorption rate information, and brightness of the color is varied in a direction of another axis according to the elasticity information.

The color map may be composed in a way that the color is varied in a direction of one axis according to the elasticity information, and brightness of the color is varied in a direction of another axis according to the optical absorption rate information.

The image generating unit may be configured to generate a photo-acoustic image based on the acoustic wave data, and to map a different color to a tissue that forms the photo-acoustic image according to the elasticity information of the tissue.

The image generating unit may be configured to map a color only with respect to a predetermined area that is set as an area of interest from the photo-acoustic image by a user.

The image generating unit may be configured to generate a photo-acoustic image based on the acoustic wave data, and to display the elasticity information, which is calculated from the elasticity information generating unit, on a specified area of the photo-acoustic image.

The image generating unit may be configured to display the elasticity information only with respect to a predetermined area that is set as an area of interest from the photo-acoustic image by a user.

The elasticity information generating unit may be configured to calculate a strain of the subject based on the first acoustic wave data and the second acoustic wave data, and to calculate a coefficient of elasticity of the subject based on a size of the stress applied to the subject and the calculated strain.

In accordance with another aspect of the present disclosure, an ultrasound imaging apparatus includes a probe, a data acquisition unit, and an elasticity information generating unit. The probe may be configured to radiate light having a particular wavelength component to a subject in a state when a stress is applied to the subject and in a state when a stress is not applied to the subject, and configured to receive a first acoustic wave signal that is generated when a stress is not applied to the subject and a second acoustic wave signal that is generated when a stress is applied to the subject. The data acquisition unit may be configured to acquire a first acoustic wave data and a second acoustic wave data that each display optical absorption rate information about the subject, by processing the first acoustic wave signal and the second acoustic wave signal that are received from the probe. The elasticity information generating unit may be configured to calculate elasticity information about the subject by comparatively analyzing the first acoustic wave data and the second acoustic wave data.

The ultrasound imaging apparatus may further include an image generating unit and a display unit. The image generating unit may be configured to generate a photo-acoustic image with respect to the subject by using the acoustic wave data acquired from the data acquisition unit. The display unit may be configured to display the photo-acoustic image generated from the image generating unit together with the elasticity information calculated from the elasticity information generating unit.

In accordance with another aspect of the present disclosure, a method of displaying an ultrasound image may be performed to enhance the accuracy and the efficiency of a diagnosis by simultaneously obtaining photo-acoustic information and elasticity information about a subject using an ultrasound imaging apparatus, and by generating and displaying a single image having both information. A first acoustic wave signal may be received by radiating light having a particular wavelength component to a subject in a state when a stress is not applied to the subject. A second acoustic wave signal may be received by radiating the light to the subject in a state when a stress is applied to the subject. A first acoustic wave data and a second acoustic wave data that represent optical absorption rate information about the subject may be acquired by processing the first acoustic wave signal and the second acoustic wave signal.

Elasticity information about the subject may be calculated by comparatively analyzing the first acoustic wave data and the second acoustic wave data. A single image having both of the optical absorption rate information, which is expressed as the acoustic wave data, and the calculated elasticity information are generated and displayed.

The generating of the single image having both of the optical absorption rate information and the calculated elasticity information may represent mapping a color to a tissue, which forms the image, the color corresponding to the tissue according to the optical absorption rate information and the elasticity information of the tissue.

The generating of the single image having both of the optical absorption rate information and the calculated elasticity information may be performed by using a color map.

The color map may be composed in a way that the color in a direction of one axis is varied according to the optical absorption rate information, and the color in a direction of another axis is varied according to the elasticity information.

The color map may be composed in a way that the color is varied in a direction of one axis according to the optical absorption rate information, and brightness of the color is varied in a direction of another axis according to the elasticity information.

The color map may be composed in a way that the color is varied in a direction of one axis according to the elasticity information, and brightness of the color is varied in a direction of another axis according to the optical absorption rate information.

In accordance with another aspect of the present disclosure, a method of displaying an ultrasound image may include receiving a first acoustic wave signal by radiating light having a particular wavelength to a subject in a state when a stress is not applied to the subject. A second acoustic wave signal may be received by radiating the light to the subject in a state when a stress is applied to the subject. A first acoustic wave data and a second acoustic wave data may be acquired by processing the first acoustic wave signal and the second acoustic wave signal. Elasticity information with respect to the subject may be calculated by comparatively analyzing the first acoustic wave data and the second acoustic wave data.

In accordance with another aspect of the present disclosure, a method of displaying an ultrasound image may include transmitting light of a first wavelength to a subject when a stress is not applied to the subject and when a stress is applied to the subject and receiving a first acoustic wave signal and a second acoustic wave signal corresponding to the transmitting of the light when the stress is not applied to the subject and when the stress is applied to the subject. Signal processing may be performed on the first acoustic wave signal and the second acoustic wave signal to obtain optical absorption rate information of the subject, and the first acoustic wave signal and the second acoustic wave signal may be analyzed by calculating distances between time windows of the first acoustic wave signal and the second acoustic wave signal, to obtain a strain of the subject. The method may further include calculating elasticity information with respect to the subject using the obtained strain and generating a single image including optical absorption rate information and elasticity information with respect to the subject.

Additionally, a stress applied to the subject may be measured using a sensor, wherein calculating of the elasticity information with respect to the subject may use the measured stress.

Further, generating a single image may include generating a photo-acoustic image in grayscale using the optical absorption rate information of the subject and performing color mapping of the elasticity information to a predetermined portion of the photo-acoustic image using the elasticity information.

According to the ultrasound imaging apparatus and the method of displaying an ultrasound image, the photo-acoustic information and the elasticity information with respect to the subject are simultaneously acquired, so that the test time and the cost of the test may be reduced.

In addition, a single image having the photo-acoustic information and the elasticity information with respect to the subject are generated and displayed, so that the accuracy of a diagnosis may be enhanced, and since no separate image matching process is needed, an error associated with the matching may be avoided and thus prevented.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 1 is a control block diagram with respect to an ultrasound imaging apparatus in accordance with one embodiment of the present disclosure.

DETAILED DESCRIPTION

Figure 2A:
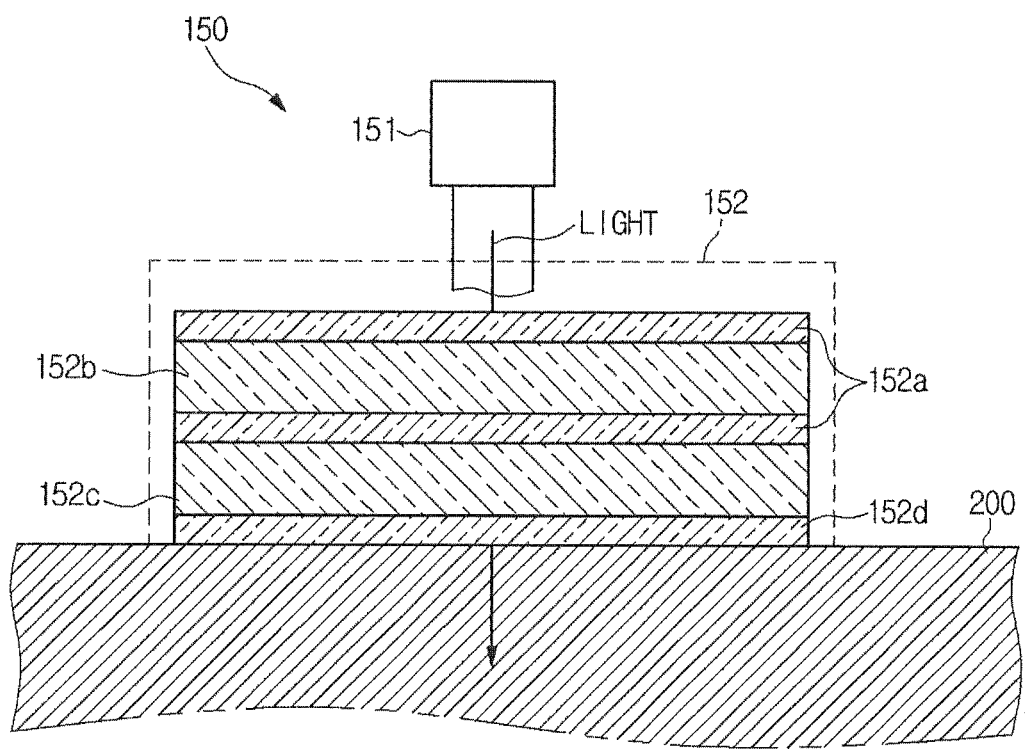
FIGS. 2A and 2B are views showing a shape of a probe that is applicable to one embodiment of the present disclosure.

Reference will now be made in detail to the embodiments of the present disclosure, examples of which are illustrated in the accompanying drawings, wherein like reference numerals refer to like elements throughout.

FIG. 1 is a control block diagram with respect to an ultrasound imaging apparatus in accordance with one embodiment of the present disclosure.

Referring to FIG. 1, an ultrasound imaging apparatus in accordance with one embodiment of the present disclosure includes a light transmitting unit 112 to transmit light having a particular wavelength to a subject, an image data generating unit 114 to generate an image data from an acoustic wave signal that is generated at the subject, a control unit 110 to control the light transmitting unit 112 and the image data generating unit 114, and a display unit 190 to display an image generated at the image data generating unit.

The light transmitting unit 112 is configured to allow a subject 200 to generate an acoustic wave by radiating the light having a particular wavelength at the subject, and includes a light source unit 120, an optical multiplexer unit 130, an optical waveguide unit 140, and a light radiating unit 151.

The light source unit 120 may include a plurality of light sources generating rays having different wavelengths. Each light source may include a light emitting device such as a semiconductor laser (LD), a light-emitting diode (LED), a solid laser, or a gas laser configured to generate a particular wavelength component or monochromatic light including a particular wavelength component. As one example, in a case when the concentration level of hemoglobin of a subject is needed to be measured, a laser beam having a pulse width of about 10 nsec may be generated by using a Nd:YAG laser (a solid laser) having a wavelength of about 1,000 nm or a He—Ne gas laser having a wavelength of about 633 nm. The concentration level of the hemoglobin inside a body may be provided with a different optical absorption characteristic depending on the type of the hemoglobin, but in general, the hemoglobin inside a body absorbs light between about 600 nm and about 1000 nm. A small-size light-emitting device, such as a LD or a LED, which is composed of InGaAlP when the light emitting wavelength is between about 550 nm and about 650 nm, GaAlAs when the light emitting wavelength is between about 650 nm and about 900 nm, or InGaAs or InGaAsP, when the light emitting wavelength is between about 900 nm and about 2300 nm, may be used. In addition, an OPO (Optical Parametrical Oscillators) laser capable of changing the wavelength by using a non-linear photonic crystal may be used.

The optical multiplexer unit 130 may be configured to multiplex the rays, which are provided with different wavelengths, generated at a plurality of light sources on the same optical axis, and may include a spectrum lens to convert the rays into the parallel rays, and a rectangular prism or a dichromatic mirror to align optical axes of the rays. However, if the light source is the OPO laser capable of continuously changing wavelengths, the optical multiplexer unit 130 may be omitted.

The optical waveguide unit 140 guides an optical output from the optical multiplexer unit 130 to a subject 200. Since a plurality of optical fibers or a plurality of thin film optical waveguides may be used, light may supplied from any one or more of the optical fibers or the thin film optical waveguides, which may be selected.

The light radiating unit 151 radiates light to a subject by sequentially selecting the plurality of optical fibers that may be arranged at the optical waveguide unit 140. The light radiating unit 151 is positioned at an output end of the optical waveguide unit 140, and is integrally provided with a signal detecting unit 152, which will be described later, and with a probe 150.

When light having a particular wavelength is radiated to a subject 200 from the light radiating unit 151, a thermo-elastic expansion occurs at a tissue that absorbs the light, a temporary acoustic pressure is generated, and thus the tissue discharges an acoustic wave. Here, the acoustic wave may be an ultrasound having a frequency band between about 20000 hz and about 50000 hz.

The image data generating unit 114 is configured to generate image data by receiving an acoustic wave signal that is discharged from the tissue of the subject 200, and includes the signal detecting unit 152, a data acquisition unit 170, an elasticity information generating unit 160, and an image generating unit 180.

The signal detecting unit 152, by detecting the acoustic wave signal being discharged from a subject, converts the acoustic wave signal into the electrical signal, and transmits the electrical signal to the data acquisition unit 170. For the conversion into the electrical signal, the signal detecting unit 152 may include a plurality of piezo-electric devices or a plurality of conversion devices. The conversion devices may be arranged, for example, in a one dimensional form or a two dimensional form. The signal detecting unit 152, along with the light radiating unit 151, composes the probe 150, and may be disposed in the form of a matrix so that more than two units of the light radiating unit 151 and the signal detecting unit 152 may simultaneously perform a multipoint monitoring.

Figure 2B:
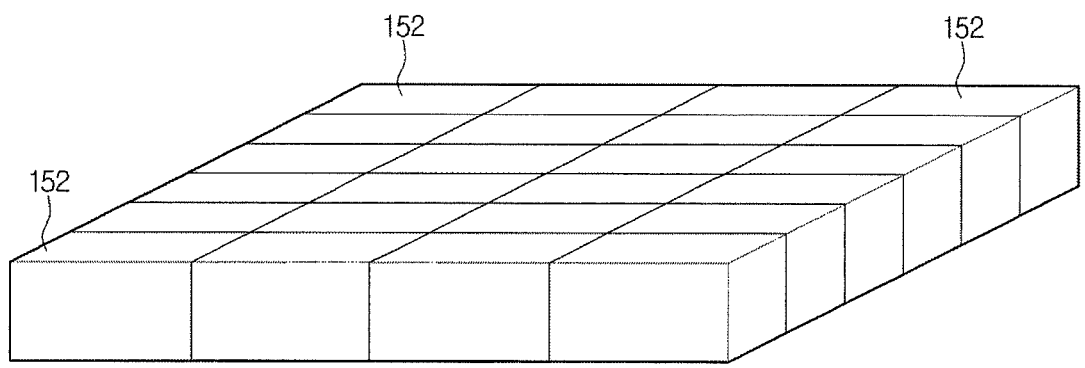

FIGS. 2A and 2B are views showing a shape of a probe 150 that is applicable to one embodiment of the present disclosure. As illustrated in FIG. 2A, by having the signal detecting unit 152 coupled to a front surface of the light radiating unit 151, the light from the light radiating unit 151 may be radiated at a subject 200 after passing through the signal detecting unit 152. The signal detecting unit 152 may include a conversion device 152b. The conversion device 152b may include a PZNT single crystal.

An electrode 152a may be mounted at an upper surface and at a lower surface of the conversion device 152b. The electrode 152a may be configured to supply a driving signal to the conversion device 152b and to receive a reception signal. At the electrode 152a mounted at the lower surface of the conversion device 152b, an acoustic matching layer 152c may be disposed which is configured to efficiently perform the transmission/reception of the acoustic wave. The acoustic matching layer 152c may employ transparent epoxy resin. Optically transparent silicon resin may be used as a protective film 152d. The protective film 152d may be disposed at a lower surface of the acoustic matching layer 152c such that it covers the acoustic matching layer 152c.

The structure having the light, which is passed through the light radiating unit 151, and passes through the signal detecting unit 152, may be easily integrated and miniaturized. Thus, in order for more than two units of the light radiating unit 151 and the signal detecting unit 152 to simultaneously perform a multipoint monitoring, as illustrated in FIG. 2B, the more than two units of the light radiating unit 151 and the signal detecting unit 152 may be disposed in the form of a matrix as shown in FIG. 2B. In addition, more than two units of the light radiating unit 151 may be coupled to a single unit of the signal detecting unit 152.

Figure 3A:
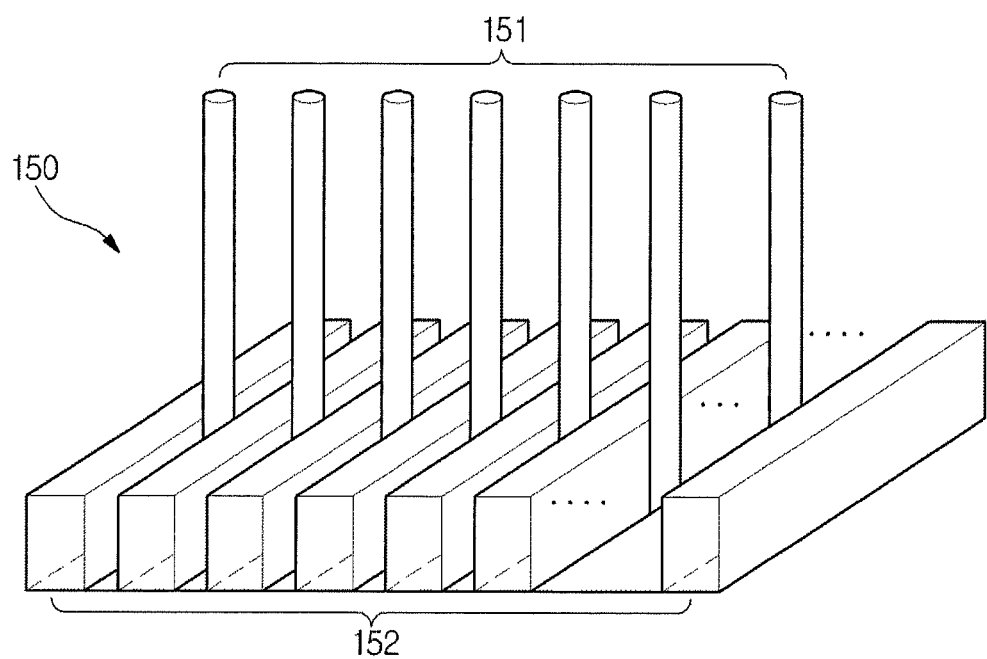
FIGS. 3A and 3B are views showing another shape of a probe that is applicable to one embodiment of the present disclosure.
Figure 3B:
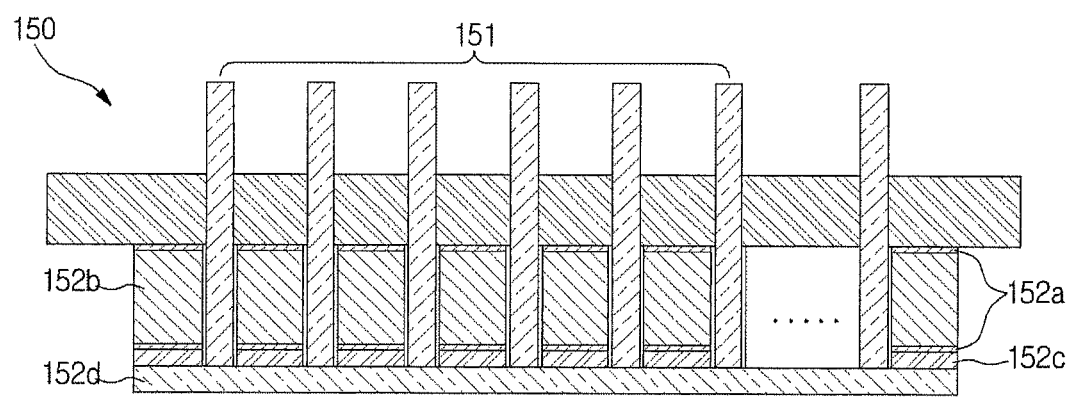

FIGS. 3A and 3B are views showing another shape of a probe that may be applicable to one embodiment of the present disclosure. As illustrated in FIG. 3A, the light radiating unit 151 may be disposed in between each of the signal detecting units 152. The cross section of the probe 150 of FIG. 3A dissected in a lengthways direction of the light radiating unit 151 is illustrated in FIG. 3B. As illustrated in FIG. 3B, the signal detecting unit 152 may be arranged in one direction, while the light radiating unit 151 is coupled in a way to be positioned in between each of the signal detecting units 152. For example, there may be more than one light radiating unit 151 which is disposed between each of the signal detecting units 152. The lowest surface of the probe 150 may be covered with the protective film 152d.

FIG. 2 and FIG. 3 are merely example embodiments of the probe 150 which are capable of transmitting light having a particular wavelength and of receiving the acoustic wave, particularly, the ultrasound signal, generated from a subject. Thus, the probe 150 used in the example embodiments described above are not limited thereto, and other probe configurations may be utilized and sufficient as long as the structure is capable of transmitting light and receiving an acoustic wave.

The data acquisition unit 170 obtains acoustic wave data, representing the optical absorption rate of a subject, from the acoustic wave signal detected by the signal detecting unit 152. By disposing a signal amplifier in between the signal detecting unit 152 and the data acquisition unit 170, the acoustic wave signal that is converted into the electrical signal may be amplified at a sufficient amplitude.

The data acquisition unit 170 may include a data collecting unit 172 and a signal processing unit 171. The data collecting unit 172 digitalizes and collects the acoustic wave signal that is converted into the electrical signal, and the signal processing unit 171, by performing the processing of various signals at the acoustic wave signal, generates the acoustic wave data that includes the light absorption rate information of a subject. Other properties may be obtained from the acoustic wave signal, including properties regarding scattering, for example a scattering coefficient or an index of refraction.

Since the elasticity information generating unit 160 calculates the elasticity information of a subject from the acoustic wave data that is generated by the data acquisition unit 170, the elasticity information being calculated here may be the coefficient of elasticity or the modulus of elasticity.

The image generating unit 180 generates a single image that includes both of the optical absorption rate information and the elasticity information with respect to a subject 200, and displays this information through a display unit 190. The detailed description will be provided later.

Hereinafter, an operation of an ultrasound imaging apparatus generating elasticity information in accordance with one embodiment of the present disclosure will be described in detail.

Figure 4A:
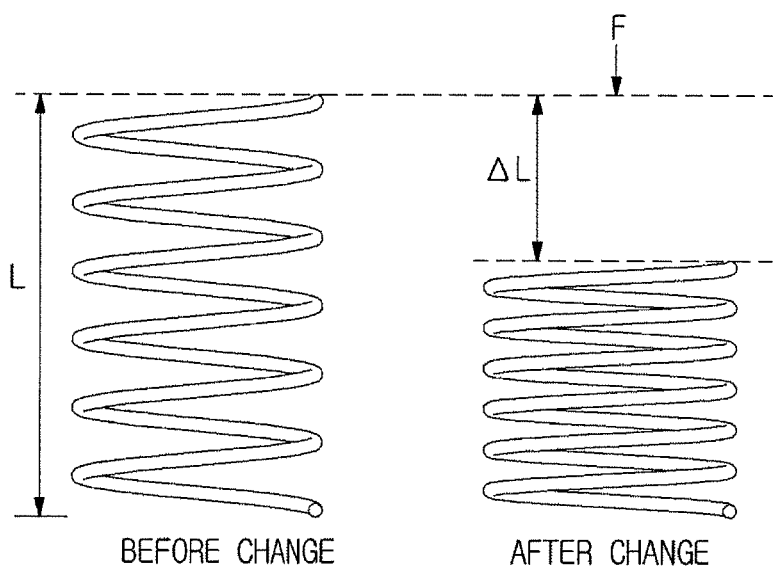
FIG. 4A is a view illustrating a spring model of coefficient of elasticity.
Figure 4B:
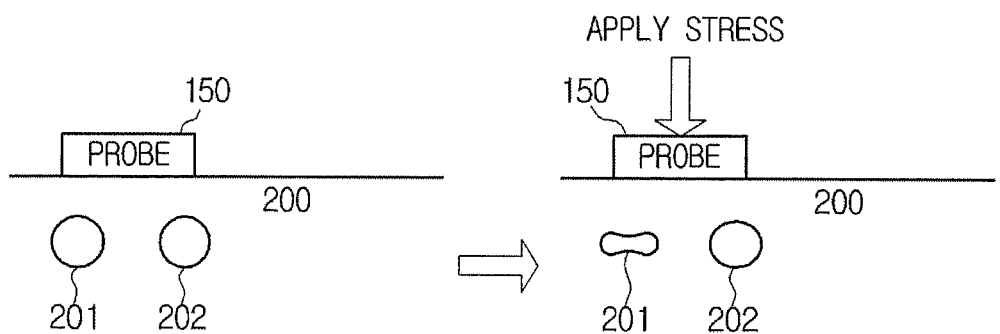
FIG. 4B is a view illustrating the spring model of coefficient of elasticity applied to a tissue of a subject.

FIG. 4A illustrates a spring model provided with a coefficient of elasticity, and FIG. 4B is a view showing the spring model provided with a coefficient of elasticity applied to a tissue of a subject.

Referring to FIG. 4A, the force 'F' needed to compress a spring by a certain length, is in proportion to the coefficient of elasticity of the spring. That is, assuming that the force applied to a unit area is referred to as a stress (stress, a), and the degree of deformation made by the stress applied is referred to as a strain (strain, E), the coefficient of elasticity E is defined as in the [Mathematical Formula]:

$$E = \sigma/\epsilon$$

$$\sigma = F/A$$

$$\epsilon = \Delta L/L \qquad \text{[Mathematical Formula 1]}$$

Here, 'A' is referred to as an area at which the stress is applied, 'L' is referred to as the length of the spring when the stress is not applied, and '$\Delta L$' is referred to as the change in the length of the spring according to the stress being applied. That is, $\Delta L$ may be equivalent to the total length of the spring when stress is not applied less the total length of the spring when stress is applied.

Referring to FIG. 4B, the spring model of the coefficient of elasticity may be applied to the tissue of a subject. Even when the same size of the stress is applied to a subject, a tissue of cancer 202, which is hard, is provided with a smaller strain (i.e., degree of deformation) when compared to a normal tissue 201. Thus, the coefficient of elasticity of the tissue of cancer 202 is provided with a larger value when compared to the coefficient of elasticity of the normal tissue 201, and an imaging method utilizing such a method includes the ultrasound elasticity imaging method. The modulus of elasticity may be calculated as the stress divided by the strain. Thus, a higher elastic modulus implies a stiffer material relative to a lower elastic modulus value which implies that the material may be more easily deformed. For example, a tissue of cancer 202 may have a higher modulus of elasticity than a normal tissue 201.

A conventional ultrasound elasticity imaging method may include a state when a stress is not applied to a test portion of a subject and an ultrasound wave is transmitted to obtain a first ultrasound echo signal, and a state when a stress is applied to the test portion of the subject, and an ultrasound wave is transmitted to obtain a second ultrasound echo signal. The first and second ultrasound echo signals may be used to calculate the strain of a tissue that is present at the test portion of the subject. However, at the ultrasound imaging apparatus in accordance with one embodiment of the present disclosure, a light having a particular wavelength may be radiated to a test portion of a subject, and the elasticity information of the tissue may be calculated by receiving an acoustic wave signal, particularly an ultrasound signal, generated from the subject.

In order to obtain the elasticity information of a subject, free-hand elastography may be used. The free-hand elastography is an elasticity imaging method that is increasingly being used, and involves applying a stress to a subject by applying a pressure at the probe 150 directly by a user. That is, the user may exert pressure to the probe 150 which is in contact with the subject. Other methods which may be used may include applying a stress to a subject by using a vibrating body provided at the probe 150 without having a user directly apply a stress. That is, a vibrating body provided at the probe 150 may be used to exert pressure to the subject. However, in the embodiments to be described hereinafter, the probe 150 is directly pressed by a user.

In detail, in one embodiment of the present disclosure, in a state when the probe 150 is not directly pressed by a user, by having the probe 150 make contact with a test portion of a subject, the transmission of the light, as well as the reception of the acoustic wave signal occurs. In addition, in a state when the probe 150 is pressed by a user, that is, in a state when a stress is applied to the test portion of a subject, the transmission of the light, as well as the reception of the acoustic wave signal also occur.

Figure 5:
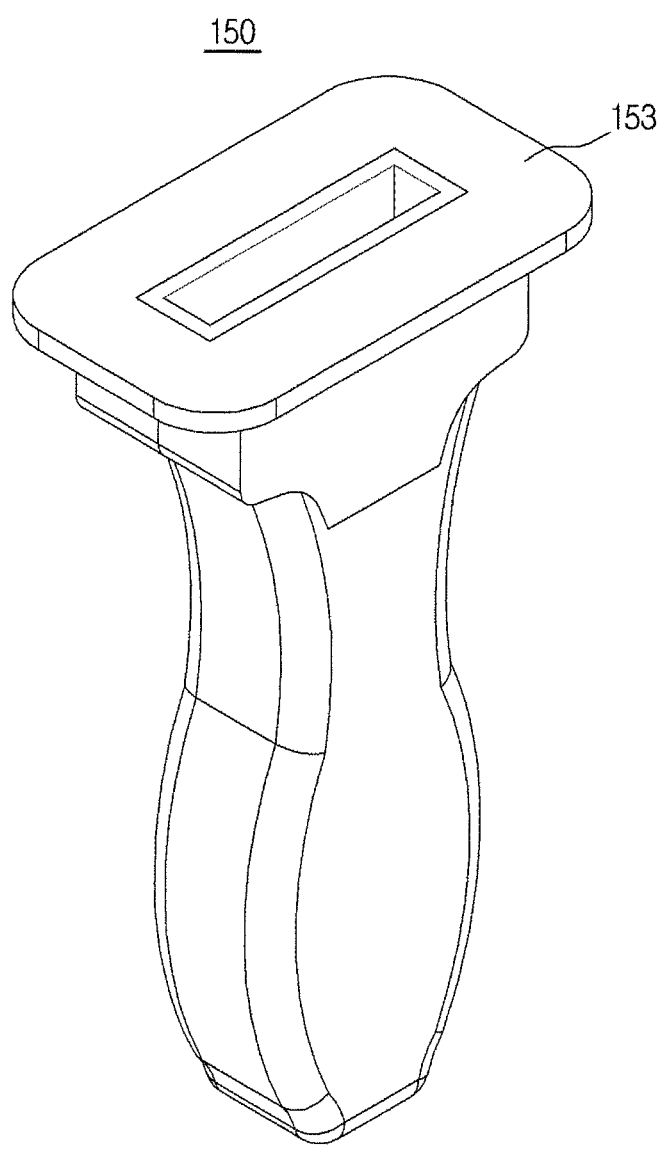
FIG. 5 is a view illustrating a probe provided with a stress delivering unit.

As illustrated in FIG. 5, since the probe 150 may be provided with a stress delivering unit 153, the stress delivering unit 153 may be provided with an area that is capable of applying a stress on the test portion of a subject. The structure of the stress delivering unit 153 is not limited to the configuration as shown in FIG. 5, but instead may take various shapes.

The data collecting unit 172, by collecting a first acoustic wave signal, which is received in a state when a stress is not applied to a subject, and a second acoustic wave signal, which is received in a state when a stress is applied to a subject, transmits the collected first and second acoustic wave signals to the signal processing unit 171.

The signal processing unit 171 generates first acoustic wave data by processing the first acoustic wave signal, and generates second acoustic wave data by processing the second acoustic wave signal. The generated acoustic wave data include the optical absorption rate information of a subject. Here, the subject includes internal tissues that compose the subject. The generating of the acoustic wave data by processing the acoustic wave signal received from the subject is a technology that is publicly known, and thus the detailed description thereof will be omitted. The generated first acoustic wave data and the second acoustic wave data are transmitted to the elasticity information generating unit 160.

As already described in FIG. 4B, in a state when a stress is applied on a subject, the strain may be varied depending on the stiffness of the tissue of the subject. Thus, by analyzing the first acoustic wave data and the second acoustic wave data, the coefficient of elasticity of the tissue may be obtained.

At the elasticity information generating unit 160, the elasticity information may be calculated by using the strain of the tissue that is present on the test portion of a subject and the size or magnitude of the stress applied on the tissue. The size of the strain may be obtained by using a method such as an auto correlation, and hereinafter, the description of the obtaining of the strain will be made in relation to using the auto correlation at the elasticity information generating unit 160.

Figure 6:
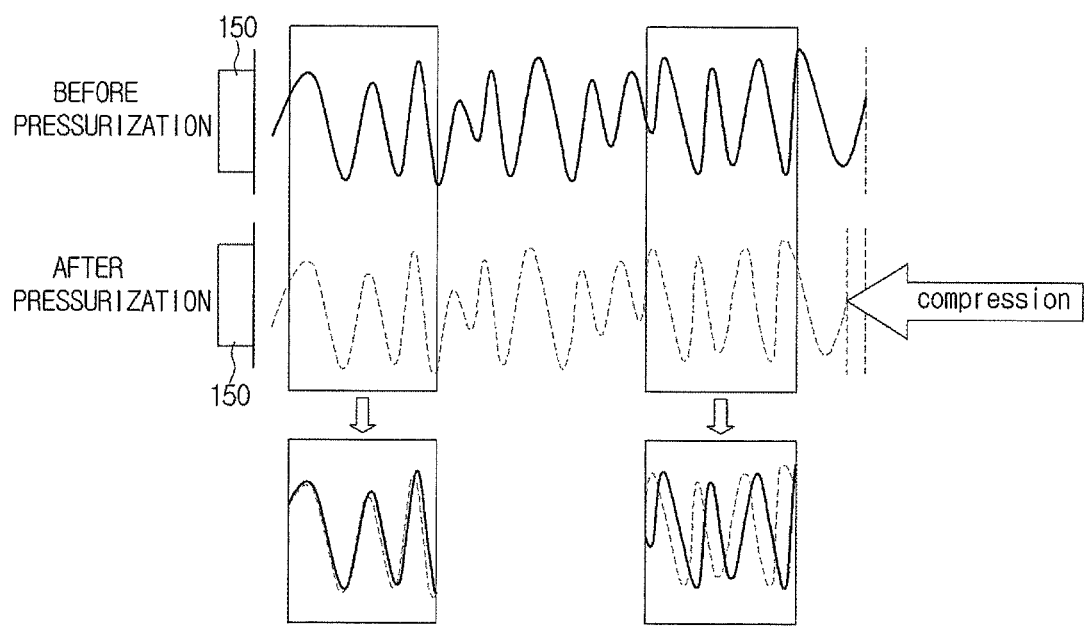
FIG. 6 is a view showing the shapes of acoustic wave signals that are each generated from a subject before/after the application of a stress.

FIG. 6 is a view showing the shapes of acoustic wave signals that are each generated from a subject before and after the application of a stress. As illustrated in FIG. 6, when a stress is applied by pressurizing the probe 150, a substance, such as the tissue disposed inside a subject, that discharges an acoustic wave by absorbing optical energy is moved in a direction of the compression. Further, when a stress is applied an acoustic wave signal may have a reception time that is moved or shifted when compared to a signal prior to the stress being applied. Thus, by calculating the movement between the two signals, the displacement of the tissue may be obtained.

Figure 7:
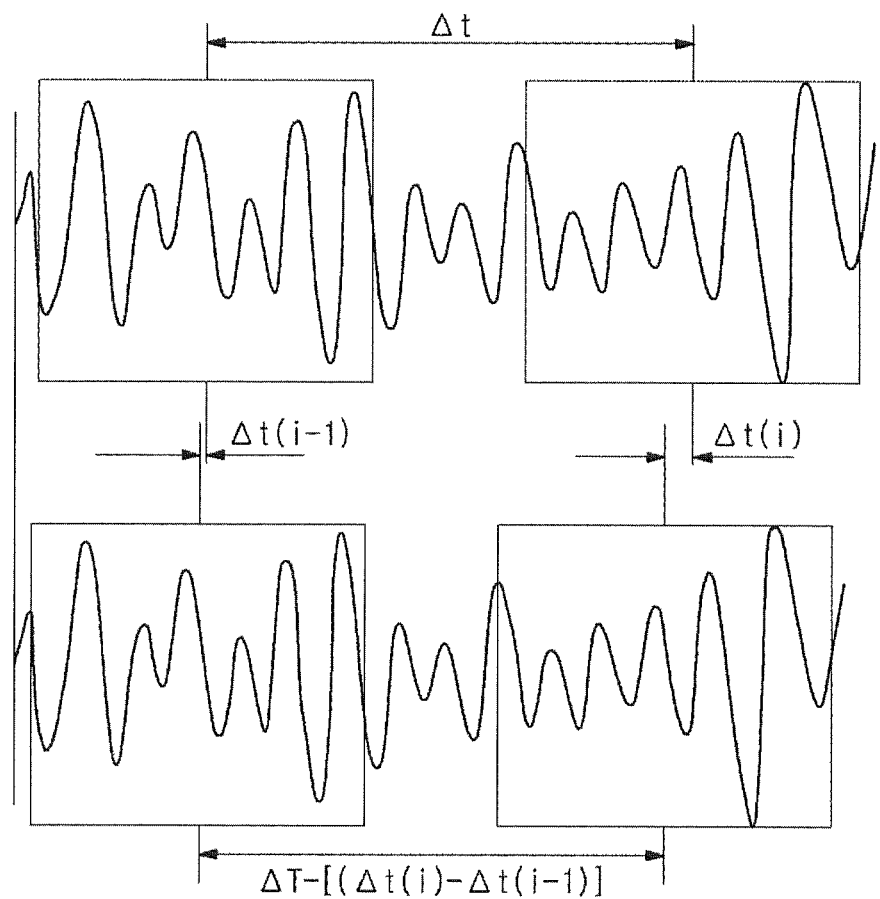
FIG. 7 is a view of a window applied to a portion of the acoustic wave signal that is generated at a subject.

FIG. 7 is a view of a window applied to a portion of the acoustic wave signal that is generated at a subject.

Referring to FIG. 7, a strain needed to calculate the elasticity information may be obtained by the distance change between two adjacent windows that are taken at the signal. The distance between two windows after the pressurization, the two windows being provided with the same data as the windows prior to the pressurization, is reduced when compared to the distance prior to the pressurization. Assuming that the distance between the two windows is referred to as $\Delta T$ prior to the pressurization, the positions of the two windows are moved by $\Delta t(i-1)$ and $\Delta t(i)$, respectively, after the pressurization, the strain 's(i)' may be expressed as in the Mathematical Formula 2:

$$s(i) = \Delta L/L = \{\Delta t(i) - \Delta t(i-1)\}/\Delta T \qquad \text{[Mathematical Formula 2]}$$

The above formula is expressed in the form of a differential of the displacement, and the method of obtaining the strain is referred to as the gradient method.

A method of estimating the displacement in calculating a strain may include a method of using RF data according to the data being used, a method using IQ data at a low frequency band, or a method using a speckle pattern of a B-mode image. These methods may calculate a displacement by calculating the correlation of the signals before and after the pressurization.

The methods of calculating the strain according to the above embodiments of the present disclosure, and the present disclosure are not limited thereto.

In order to calculate the elasticity information according to the degree of the strain of a tissue in a case when a stress is applied to a subject and in a case when a stress is not applied to a subject, the size of the stress applied to the subject need not be obtained or calculated.

Figure 8:
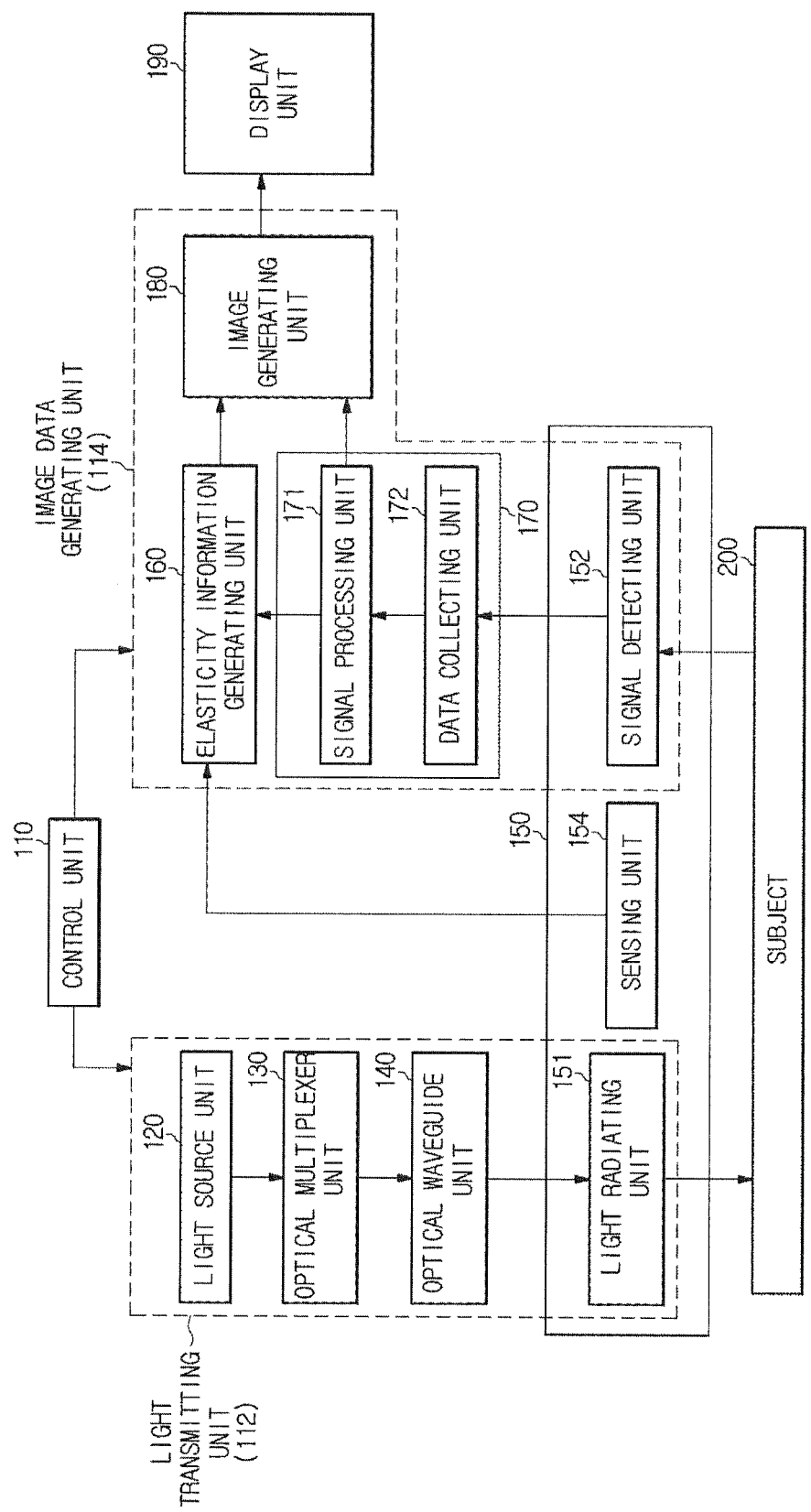
FIG. 8 is a control block diagram of an ultrasound imaging apparatus capable of measuring the size of the stress applied to a subject.

FIG. 8 is a control block diagram of an ultrasound imaging apparatus capable of measuring the size of the stress applied to a subject.

Since the distribution of the stress at a location inside a subject may not precisely be measured, the elasticity may be estimated by using only the strain on the assumption that the distribution of the stress is uniform. However, as illustrated on FIG. 8, the stress applied to a subject may be able to be measured by having a sensor unit 154 at the probe 150.

The sensor unit 154 may include at least one of a stress sensor to directly measure the stress applied to the subject, and an acceleration sensor to measure the acceleration speed of the probe 150.

The measurement result of the sensor unit 154 may be transmitted to the elasticity information generating unit 160. In a case when the sensor unit 154 is the stress sensor, by using the size of the stress measured and the strain calculated by the elasticity information generating unit 160, the elasticity information of a subject may be calculated. In a case when the sensor unit 154 is the acceleration sensor, by using the acceleration speed measured at the acceleration sensor, the mass of the probe 150, and the contact area of the probe 150 with the subject, the stress applied to the subject may be calculated.

As described above, when the acoustic wave data is obtained at the data acquisition unit 170 and the elasticity information of a subject is calculated at the elasticity information generating unit 160, a single image having the optical absorption rate and the elasticity information of the subject is generated at the image generating unit 180, so that the single image may be displayed through the display unit 190. An operation of generating an image at the image generating unit 180 will be described in detail.

Figure 9A:
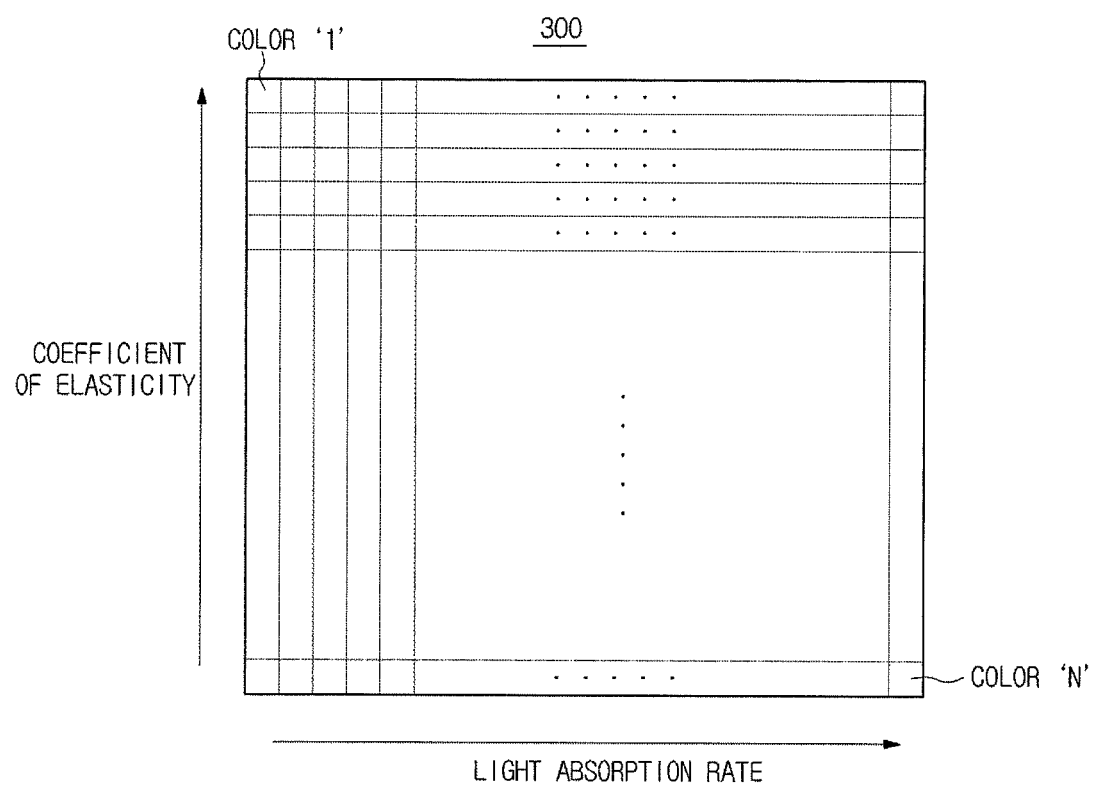
FIG. 9A is a view illustrating an example of a color map that may be used at an image generating unit 180 of an ultrasound imaging apparatus in accordance with one embodiment of the present disclosure.
Figure 9B:
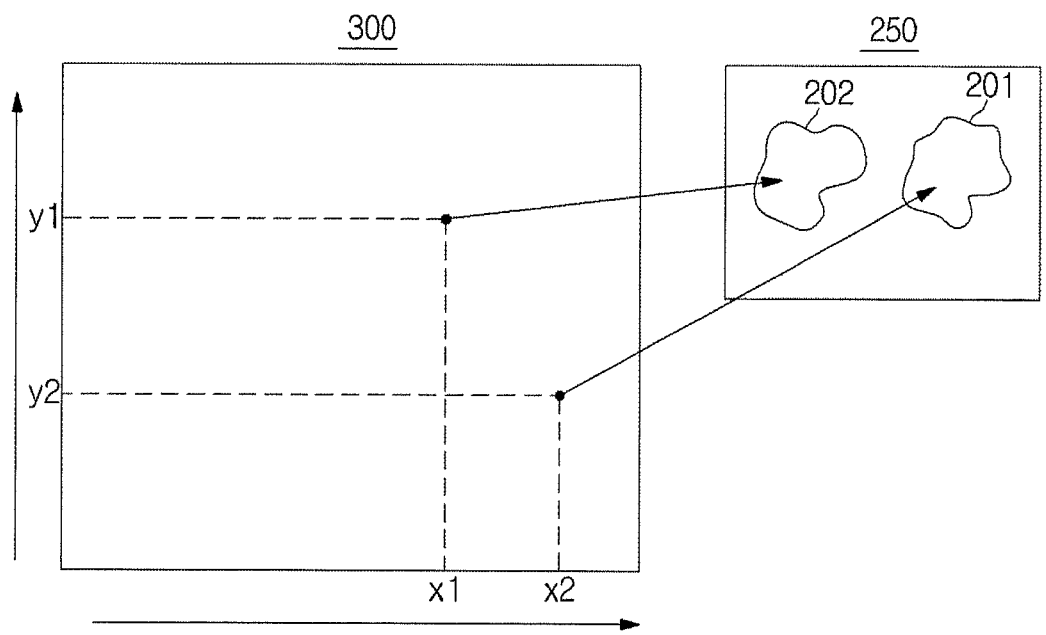
FIG. 9B is a color mapping screen using the color map of FIG. 9A.

FIG. 9A is a view illustrating an example of a color map that may be used at an image generating unit 180 of an ultrasound imaging apparatus in accordance with one embodiment of the present disclosure. FIG. 9B is a color mapping screen using the color map of FIG. 9A.

The image generating unit 180, in order to include the information on the optical absorption and the elasticity of a subject on a single image, may use a color map, as illustrated in FIG. 9A.

The color map 300 in the present embodiment may be composed in the form of a two-dimensional matrix, as each of the colors from the color '1' to the color 'N' that corresponds to each block shows a different color that is different than each other, and in a case when a RGB color map is being used, the 'N' may be expressed as a number less than or equal to 16,777,216. That is, the number 16,777,216 corresponds to the number of colors that may be represented in a color palette, and is sometimes referred to as a 24 bit "true color" image. The number of the colors and the types of the colors being used at the color map may be predetermined by a user. The disclosure is not limited however to N being less than or equal to 16,777,216, and may have a value greater than 16,777,216 if desired.

Assuming that the direction in the horizontal axis of the color map corresponds to the optical absorption rate and that the direction in the vertical axis of the color map corresponds to the coefficient of elasticity of a subject, by using the coefficient of elasticity as well as the optical absorption rate of each tissue that composes an inside the subject as coordinates, a color mapping may be performed.

Referring to FIG. 9B, a tissue of cancer 202 and a normal tissue 201 are present on an image 250 generated at the image generating unit 180. The coefficient of elasticity of the tissue of cancer may correspond to y1 and the optical absorption rate of the tissue of cancer may correspond to x1, while the coefficient of elasticity of the normal tissue of cancer may correspond to y2 and the optical absorption rate of the normal tissue of cancer may correspond to x2. Thus, by using the (x1, y1) and the (x2, y2) as coordinates which correspond to the tissue of cancer 202 and the normal tissue 201, a color that corresponds to each coordinate on the color map 300 may be mapped to each tissue.

When the image is displayed at the display unit 190, a user, through the color of the each tissue, may be able to confirm the elasticity information and the optical absorption rate information. The display unit 190 may include a display device capable of displaying an image. For example, the display unit 190 may include at least one of a cathode ray display (CRT), light-emitting diode display (LED), electroluminescent display (ELD), plasma display panel (PDP), liquid crystal display (LCD), and an organic light-emitting diode display (OLED), for example. The display unit 190 may receive the image from the image generating unit 180 via a wired or wireless connection, for example.

In the embodiment of FIG. 9B, the horizontal axis of the color map 300 may be set as the optical absorption rate information and the vertical axis of the color map 300 may be set as the elasticity information. However, the opposite of the above may also be allowed, and the color mapping may be performed in pixel units.

Figure 10:
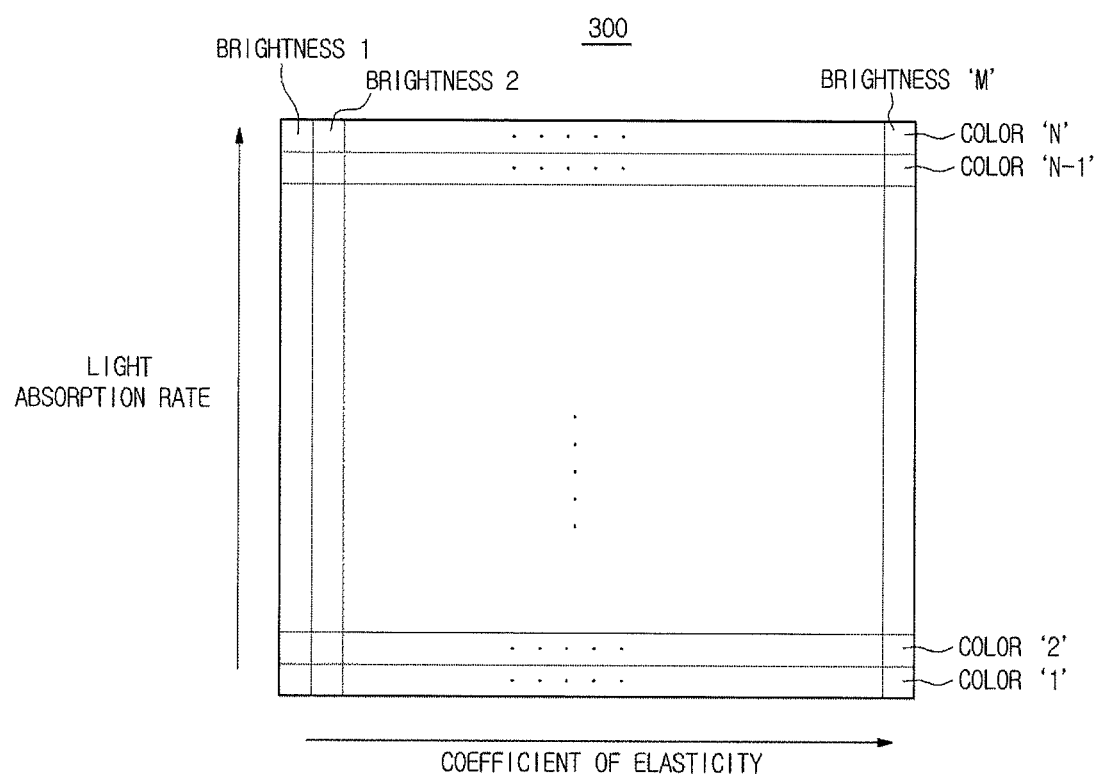
FIG. 10 is a view illustrating another example of a color map that may be used in the embodiment of the present disclosure.

FIG. 10 is a view illustrating another example of a color map that may be used in the embodiment of the present disclosure.

The color map 300 of FIG. 10 as well may be composed in the form of a two-dimensional matrix, as each column from '1' to 'N' represents a different color, while each row from '1' to 'M' represents a different brightness. The 'N' and the 'M' are integers, and may be same or different than each other. In case when a RGB color map is being used, 'N' may be expressed as an integer number having a value equal to or less than 16,777,216, and the maximum value of 'N' may vary depending on the color map that is being used. That is, the number 16,777,216 corresponds to the number of colors that may be represented in a color palette, and is sometimes referred to as a 24 bit "true color" image. The number of the colors and the types of the colors being used at the color map may be predetermined by a user. The disclosure is not limited however to N being less than or equal to 16,777,216, and may have a value greater than 16,777,216 if desired.

As the optical absorption rate corresponds to the vertical axis and the coefficient of elasticity corresponds to the horizontal axis, the color may vary depending on the optical absorption rate, while the brightness may vary depending on the coefficient of elasticity. Alternatively, having the coefficient of elasticity correspond to the vertical axis and having the optical absorption rate correspond to the horizontal axis may also be possible. In the color map of FIG. 10, as the optical absorption rate and the coefficient of elasticity are used as coordinates for each tissue or for each pixel, the mapping of the corresponding color and brightness as in FIG. 9B, may be possible.

Figure 11:
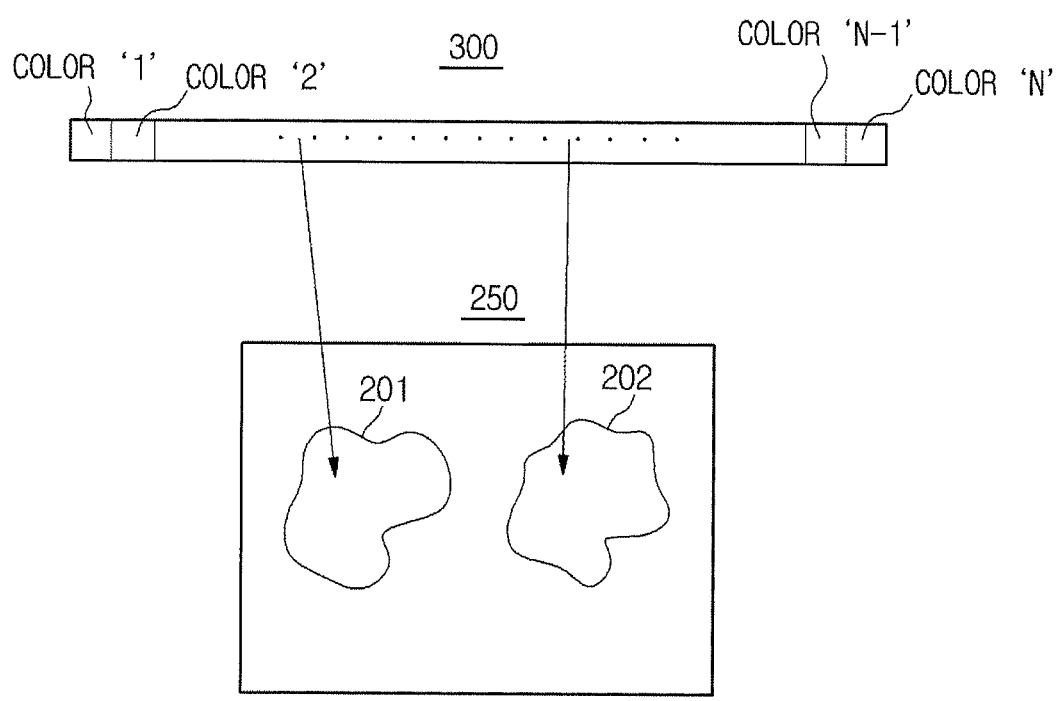
FIG. 11 is a view illustrating still another example of a color map that may be used in the embodiment of the present disclosure.

FIG. 11 is a view illustrating still another example of a color map that may be used in the embodiment of the present disclosure.

In the embodiment of FIG. 11, a one-dimensional color map may be used. In one direction of the color map, the colors from the color '1' to the color 'N' are arranged, and different colors may be matched depending on the coefficient of elasticity of the tissue. In the present embodiment, first, a photo-acoustic image, which is illustrated on FIG. 12 to be described later, is formed from the acoustic wave data obtained from the data obtaining unit 170. Then, depending on the coefficient of elasticity of each tissue calculated at the elasticity information generating unit 160, the corresponding color is mapped.

In one embodiment, the color mapping may be performed only on the area of interest that is predetermined by a user. For example, when the coefficient of elasticity is greater than a predetermined value that is set in advance, the mapping of a color that corresponds to the coefficient of elasticity may only be performed. Alternatively, the mapping of a color may be performed only on a designated area after a user designates a certain area as the area of interest by looking at the photo-acoustic image. For example, the user may select or highlight an area of a photo-acoustic image that is of interest to the user, and a color mapping may be performed only on the designated area using elasticity information.

The color maps illustrated in FIGS. 9 to 11 described above are example embodiments that may be employed in the present disclosure. However, various other methods that are capable of showing the optical absorption rate information and the elasticity information of a subject on a single image may also be employed.

Figure 12:
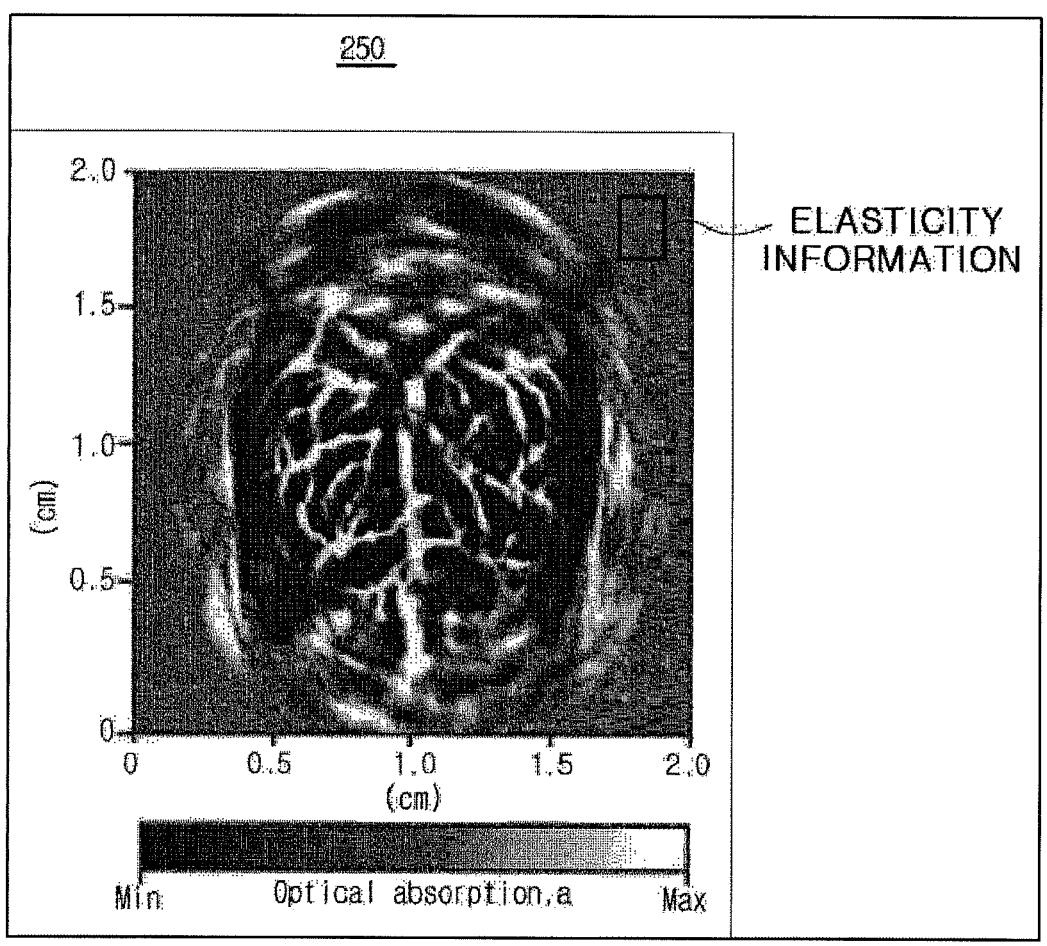
FIG. 12 is a view illustrating a different example of an image that may be generated at an image generating unit 180 of an ultrasound imaging apparatus in accordance with one embodiment of the present disclosure.

FIG. 12 is a view illustrating a different example of an image that may be generated at the image generating unit 180 of the ultrasound imaging apparatus in accordance with one embodiment of the present disclosure.

The embodiment of FIG. 12 is an image of a brain of a mouse photographed using an ultrasound imaging apparatus in accordance with one embodiment of the present disclosure. Since the acoustic wave data obtained at the data acquisition unit 170 includes the optical absorption rate information of a brain, a photo-acoustic image is generated by expressing the optical absorption rate information of a brain in grayscale, and the elasticity information calculated at the elasticity information generating unit 160 is quantified into figures to be displayed at one or more areas of the image. At this time, the elasticity information may only be displayed with respect to one or more areas of interest that is predetermined by a user.

Hereinafter, a method of displaying an ultrasound image in accordance with one embodiment of the present disclosure will be described.

Figure 13:
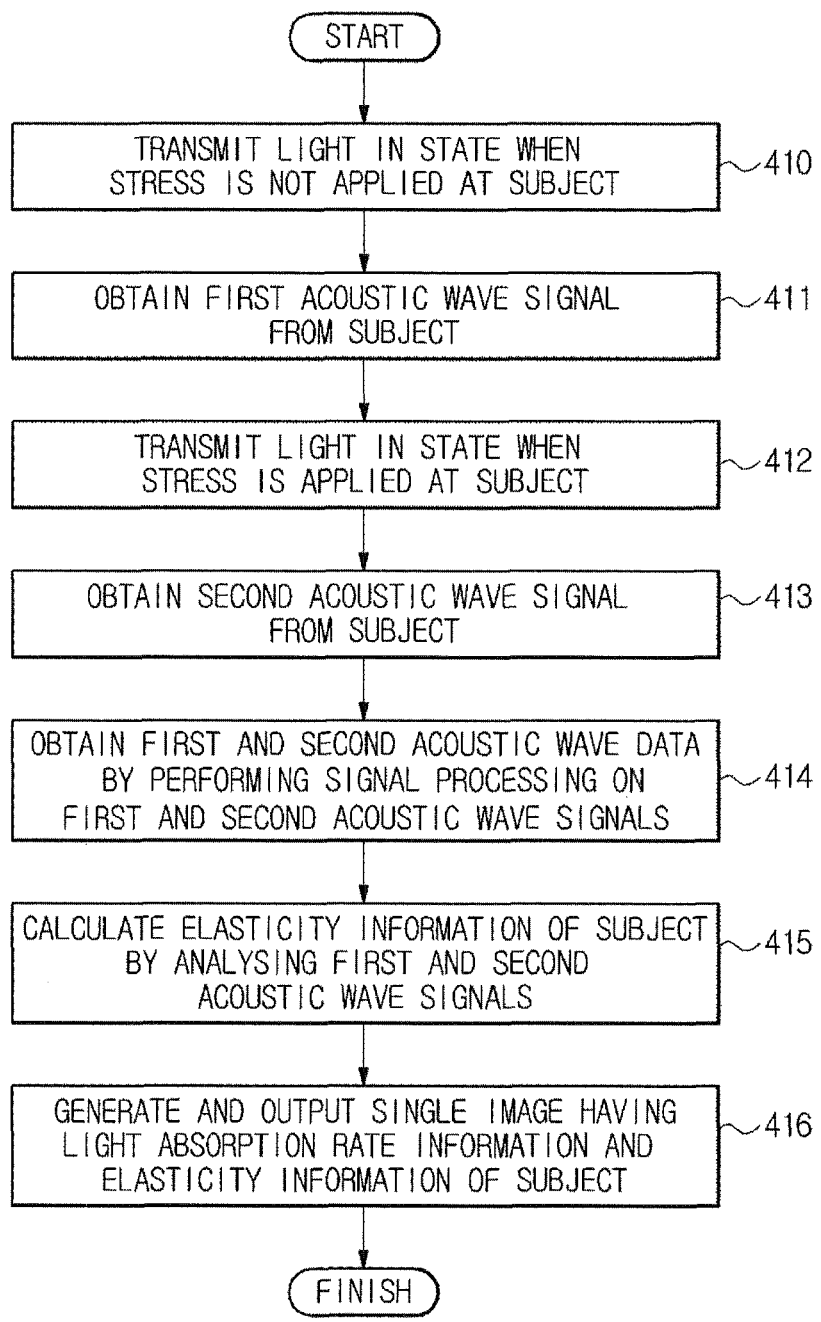
FIG. 13 is a flow chart on a method of displaying an ultrasound image in accordance with one embodiment of the present disclosure.

FIG. 13 is a flow chart on a method of displaying an ultrasound image in accordance with one embodiment of the present disclosure.

Referring to FIG. 13, initially, in a state when a stress is not applied to a subject, light having a particular wavelength is transmitted via the light radiating unit 151 included in the probe 150, for example (410). Here, the state of a stress not being applied may be referred to as the state of the probe 150 not being pressurized, while the probe 150 is in contact with the test portion of the subject, to obtain the elasticity information. That is, pressure is not applied by the user or from another source to the probe 150, however the probe 150 may be in contact with the test portion of the subject to obtain elasticity information.

The tissue inside of the subject, which absorbs the energy of the light transmitted, discharges a first acoustic wave. The probe 150 obtains a first acoustic wave signal from the subject (411).

Then, in a state of a stress being applied to the subject, light is again transmitted (412). The light transmitted at this time represents light that is configured to generate the first acoustic wave signal, that is, a light having the same wavelength as the light that was transmitted in operation 410.

The tissue inside of the subject, which absorbs the energy of the second light transmitted, discharges a second acoustic wave. The probe 150 obtains a second acoustic wave signal from the subject (413).

Next, by performing signal processing on the first acoustic wave signal and the second acoustic wave signal, first acoustic wave data and second acoustic wave data are obtained (414). In detail, the probe 150 converts the first acoustic wave signal and the second acoustic wave signal, both of which are received, into the electrical signals, and transmits the electrical signals to the data collecting unit 172. The data collecting unit 172, by converting the first acoustic wave signal and the second acoustic wave signal, which are converted into electrical signals, into the digital signals, transmits the digital signals to the signal processing unit 171, and the signal processing unit 171, by performing various signal processing with respect to the first acoustic wave signal and the second acoustic wave signal, generates the first acoustic wave data and the second acoustic wave data that include the optical absorption rate information of the subject.

Then, by analyzing the first acoustic wave data and the second acoustic wave data, the elasticity information of the subject may be calculated (415) by the elasticity information generating unit 160. Since the first acoustic wave data is obtained in a state of when a stress is not applied to the subject and the second acoustic wave data is obtained in a state of when a stress is applied to the subject, the strain of the subject may be obtained by comparatively analyzing the first acoustic wave data and the second acoustic wave data. The method of calculating the elasticity information is already described above, and thus the description of such will be omitted.

A single image having both of the optical absorption rate information and the elasticity information of the subject is generated and outputted (416). The optical absorption rate information of the subject is expressed as the acoustic wave data, and the elasticity information is calculated from the acoustic wave data. The single image having both the optical absorption rate information and the elasticity information may be generated by a method of using a color map having the optical absorption rate information and the elasticity information as the coordinate values, by a method of performing a color mapping in accordance with the elasticity information of the acoustic wave image, or by a method of displaying the coefficient of elasticity on the acoustic wave image, as discussed above regarding the descriptions corresponding to FIGS. 9 to 12.

As described above, according to the ultrasound imaging apparatus in accordance with one aspect of the present disclosure and the control method thereof, by transmitting light in each state of when a stress is applied and not applied to a subject, the optical absorption rate information and the elasticity information may be simultaneously obtained, and thereby the test time and the cost of the test may be saved. That is, an efficient test may be performed.

In addition, by showing the optical absorption rate information and the elasticity information, both of which are simultaneously obtained, on a single image, even when a user checks only the single image, the user is able to grasp the optical absorption rate information and the elasticity information, and thus a lesion may be efficiently diagnosed.

In addition, the single image is not an image obtained by matching a photo-acoustic image to an ultrasound elasticity image, both of which are separately obtained. Therefore, an error that may occur by the matching of the images may be prevented since matching is not performed.

It should be understood that the exemplary embodiments described herein should be considered in a descriptive sense only and not for purposes of limitation. Descriptions of features or aspects within each embodiment should typically be considered as available for other similar features or aspects in other embodiments.

For example, the disclosure has described one or more embodiments in which a ultrasound imaging apparatus and method of displaying an ultrasound image may be used to treat and diagnose humans. However, the ultrasound imaging apparatus and method of displaying an ultrasound image may be applied in the treatment and/or diagnosis of other life forms, including animals. The ultrasound imaging apparatus and method disclosed herein need not be limited to the medical field, and may be used in other fields, and may be used on an object in industrial applications to examine internal characteristics and structures of the object.

The terms "module", and "unit," as used herein, may refer to, but is not limited to, a software or hardware component or device, such as a Field Programmable Gate Array (FPGA) or Application Specific Integrated Circuit (ASIC), which performs certain tasks. A module or unit may be configured to reside on an addressable storage medium and configured to execute on one or more processors. Thus, a module or unit may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and modules/units may be combined into fewer components and modules/units or further separated into additional components and modules.

The ultrasound imaging apparatus and method of displaying an ultrasound image according to the above-described example embodiments may use one or more processors, which may include a microprocessor, central processing unit (CPU), digital signal processor (DSP), or application-specific integrated circuit (ASIC), as well as portions or combinations of these and other processing devices.

The method of displaying an ultrasound image according to the above-described example embodiments may be recorded in non-transitory computer-readable media including program instructions to implement various operations embodied by a computer. The media may also include, alone or in combination with the program instructions, data files, data structures, and the like. The program instructions recorded on the media may be those specially designed and constructed for the purposes of the example embodiments, or they may be of the kind well-known and available to those having skill in the computer software arts. Examples of non-transitory computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules to perform the operations of the above-described example embodiments, or vice versa.

Each block of the flowchart illustrations may represent a unit, module, segment, or portion of code, which comprises one or more executable instructions for implementing the specified logical function(s). It should also be noted that in some alternative implementations, the functions noted in the blocks may occur out of the order. For example, two blocks shown in succession may in fact be executed substantially concurrently or the blocks may sometimes be executed in the reverse order, depending upon the functionality involved.

Although a few example embodiments of the present disclosure have been shown and described, it would be appreciated by those skilled in the art that changes may be made to these embodiments without departing from the principles and spirit of the disclosure, the scope of which is defined in the claims and their equivalents.

What is claimed is:

1. An ultrasound imaging apparatus, comprising:
a probe configured to radiate light to a subject when a stress is applied to the subject and when a stress is not applied to the subject, and configured to receive a first acoustic wave signal generated when the stress is not applied to the subject and a second acoustic wave signal generated when the stress is applied to the subject;
a data acquisition unit configured to acquire first acoustic wave data and second acoustic wave data which include optical absorption rate information about the subject, based on the first acoustic wave signal and second acoustic wave signal;
an elasticity information generating unit configured to calculate elasticity information about the subject based on the first acoustic wave data and the second acoustic wave data;
an image generating unit configured to generate a single image having the optical absorption rate information and the calculated elasticity information; and
a display unit configured to display the image.

2. The ultrasound imaging apparatus of claim 1, wherein the image generating unit, by using a color map, is configured to perform a mapping of a color that corresponds to each of the optical absorption rate information and the elasticity information of a tissue that forms the image.

3. The ultrasound imaging apparatus of claim 2, wherein the mapping of the color is performed in pixel units.

4. The ultrasound imaging apparatus of claim 3, wherein the color map varies the color in a direction of a first axis according to the optical absorption rate information, and varies the color in a direction of a second axis according to the elasticity information.

5. The ultrasound imaging apparatus of claim 3, wherein the color map varies the color in a direction of a first axis according to the optical absorption rate information, and varies a brightness of the color in a direction of a second axis according to the elasticity information.

6. The ultrasound imaging apparatus of claim 3, wherein the color map varies the color in a direction of a first axis according to the elasticity information, and varies a brightness of the color in a direction of a second axis according to the optical absorption rate information.

7. The ultrasound imaging apparatus of claim 1, wherein the image generating unit is configured to generate a photo-acoustic image based on the acoustic wave data, and maps a different color to a tissue that forms the photo-acoustic image according to the elasticity information of the tissue.

8. The ultrasound imaging apparatus of claim 7, wherein the image generating unit is configured to map a color according to a predetermined area set by a user as an area of interest from the photo-acoustic image.

9. The ultrasound imaging apparatus of claim 1, wherein the image generating unit is configured to generate a photo-acoustic image based on the acoustic wave data, and displays the elasticity information, which is calculated from the elasticity information generating unit, on one area of the photo-acoustic image.

10. The ultrasound imaging apparatus of claim 9, wherein the image generating unit is configured to display the elasticity information only with respect to a predetermined area that is set as an area of interest from the photo-acoustic image by a user.

11. The ultrasound imaging apparatus of claim 1, wherein the elasticity information generating unit is configured to calculate a strain of the subject using the first acoustic wave data and the second acoustic wave data, and to calculate a coefficient of elasticity of the subject based on a size of the stress applied to the subject and the calculated strain.

12. An ultrasound imaging apparatus comprising:
a probe configured to radiate light to a subject when a stress is applied to the subject and when a stress is not applied to the subject, and configured to receive a first acoustic wave signal generated when a stress is not applied to the subject and a second acoustic wave signal generated when a stress is applied to the subject;
a data acquisition unit configured to acquire first acoustic wave data and second acoustic wave data that each include optical absorption rate information about the subject, based on the first acoustic wave signal and the second acoustic wave signal; and
an elasticity information generating unit configured to calculate elasticity information about the subject based on the first acoustic wave data and the second acoustic wave data,
an image generating unit configured to generate a photo-acoustic image with respect to the subject by using the acoustic wave data acquired from the data acquisition unit; and
a display unit configured to display the photo-acoustic image including the optical absorption rate information together with the elasticity information calculated from the elasticity information generating unit.

13. A method of displaying an ultrasound image, the method comprising:
receiving a first acoustic wave signal in response to radiating light to a subject when a stress is not applied to the subject;
receiving a second acoustic wave signal in response to radiating light to the subject when a stress is applied to the subject;
acquiring first acoustic wave data and second acoustic wave data including optical absorption rate information about the subject based on the first acoustic wave signal and the second acoustic wave signal;
calculating elasticity information about the subject based on the first acoustic wave data and the second acoustic wave data; and
generating and displaying a single image having the optical absorption rate information and the calculated elasticity information.

14. The method of claim 13, wherein the generating of the single image having the optical absorption rate information and the calculated elasticity information includes mapping a color to a tissue, which forms the image, the color corresponding to the tissue according to the optical absorption rate information and the elasticity information of the tissue.

15. The method of claim 14, wherein the generating of the single image having the optical absorption rate information and the calculated elasticity information is performed by using a color map.

16. The method of claim 15, wherein the color map varies the color in a direction of a first axis according to the optical absorption rate information, and varies the color in a direction of a second axis according to the elasticity information.

17. The method of claim 15, wherein the color map varies the color in a direction of a first axis according to the optical absorption rate information, and varies a brightness of the color in a direction of a second axis according to the elasticity information.

18. The method of claim 15, wherein the color map varies the color in a direction of a first axis according to the elasticity information, and varies a brightness of the color in a direction of a second axis according to the optical absorption rate information.

19. A method of displaying an ultrasound image, the method comprising:
receiving a first acoustic wave signal in response to radiating light to a subject when a stress is not applied to the subject;
receiving a second acoustic wave signal in response to radiating light to the subject when a stress is applied to the subject;
acquiring first acoustic wave data and second acoustic wave data based on the first acoustic wave signal and the second acoustic wave signal;
calculating optical absorption rate information with respect to the subject based on the first acoustic wave signal and the second acoustic wave signal; and
calculating elasticity information with respect to the subject based on the first acoustic wave data and the second acoustic wave data,
generating a single image including optical absorption rate information and elasticity information with respect to the subject.

20. A method of displaying an ultrasound image, the method comprising:
transmitting light of a first wavelength to a subject when a stress is not applied to the subject and when a stress is applied to the subject;
receiving a first acoustic wave signal and a second acoustic wave signal corresponding to the transmitting of the light when the stress is not applied to the subject and when the stress is applied to the subject;
performing signal processing on the first acoustic wave signal and the second acoustic wave signal, to obtain optical absorption rate information of the subject;
analyzing the first acoustic wave signal and the second acoustic wave signal by calculating distances between time windows of the first acoustic wave signal and the second acoustic wave signal, to obtain a strain of the subject;
calculating elasticity information with respect to the subject using the obtained strain; and generating a single image including optical absorption rate information and elasticity information with respect to the subject.

21. The method of claim 20, further comprising measuring a stress applied to the subject using a sensor, wherein the calculating of the elasticity information with respect to the subject uses the measured stress.

22. The method of claim 20, wherein the generating a single image comprise:

generating a photo-acoustic image in grayscale using the optical absorption rate information of the subject and color mapping the elasticity information to a predetermined portion of the photo-acoustic image using the elasticity information.

* * * * *